United States Patent
Bacher

(10) Patent No.: US 8,430,905 B2
(45) Date of Patent: *Apr. 30, 2013

(54) MEDICAL INSTRUMENT

(75) Inventor: Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 298 days.

This patent is subject to a terminal disclaimer.

(21) Appl. No.: 12/607,737

(22) Filed: Oct. 28, 2009

(65) Prior Publication Data

US 2010/0049242 A1    Feb. 25, 2010

Related U.S. Application Data

(63) Continuation of application No. 10/662,759, filed on Sep. 15, 2003, now Pat. No. 7,691,126.

(30) Foreign Application Priority Data

Sep. 14, 2002    (DE) ............... 02 020 720 U

(51) Int. Cl.
*A61B 17/28*    (2006.01)

(52) U.S. Cl.
USPC ........................................................ 606/205

(58) Field of Classification Search .............. 606/1, 190, 606/170, 205–210
See application file for complete search history.

(56) References Cited

U.S. PATENT DOCUMENTS

| | | | |
|---|---|---|---|
| 2,334,449 A | 11/1943 | Strait | |
| 2,465,783 A | 3/1949 | Beaty | |
| 3,000,658 A | 9/1961 | Sprouse | |
| 3,092,403 A * | 6/1963 | Gerdeman | 285/86 |
| 4,152,920 A | 5/1979 | Green | |
| 4,950,273 A | 8/1990 | Briggs | |
| 5,052,402 A | 10/1991 | Bencini et al. | |
| 5,282,806 A | 2/1994 | Haber et al. | |
| 5,333,964 A | 8/1994 | Thomas | |
| 5,366,477 A | 11/1994 | LeMarie, III et al. | |
| 5,469,347 A | 11/1995 | Duve et al. | |
| 5,496,347 A | 3/1996 | Hashiguchi et al. | |
| 5,603,723 A * | 2/1997 | Aranyi et al. | 606/205 |
| 5,643,294 A | 7/1997 | Tovey et al. | |
| 5,695,522 A | 12/1997 | LeMaire, III et al. | |
| 5,893,874 A | 4/1999 | Bourque et al. | |
| 6,960,210 B2 * | 11/2005 | Lands et al. | 606/50 |
| 7,083,618 B2 * | 8/2006 | Couture et al. | 606/51 |
| 2004/0218972 A1 | 11/2004 | Paulin et al. | |

FOREIGN PATENT DOCUMENTS

| | | |
|---|---|---|
| DE | 9215053 U1 | 4/1993 |
| EP | 0577423 A2 | 1/1994 |
| WO | 9641574 A2 | 12/1996 |
| WO | 0226143 A1 | 4/2002 |

* cited by examiner

*Primary Examiner* — Elizabeth Houston
(74) *Attorney, Agent, or Firm* — St. Onge Steward Johnston & Reens LLC

(57) ABSTRACT

The invention relates to a medical instrument with a shaft, a handle mounted on the proximal end of the shaft, and a tool mounted on the distal end of the shaft and capable of being activated by means of the handle, where the handle and the tool are in active connection by means of at least one activation rod. To make it possible for the tool, in particular as a one-way tool, to be secured simply and rapidly on the activation rod, the invention proposes that the tool should have a tool shaft for securing it to the activation rod and that the tool shaft and the activation rod in order to be secured to one another should have protuberances and/or recesses, which can be engaged, at least partially as a form-locking connection, with corresponding recesses or protuberances of the other respective component.

9 Claims, 3 Drawing Sheets

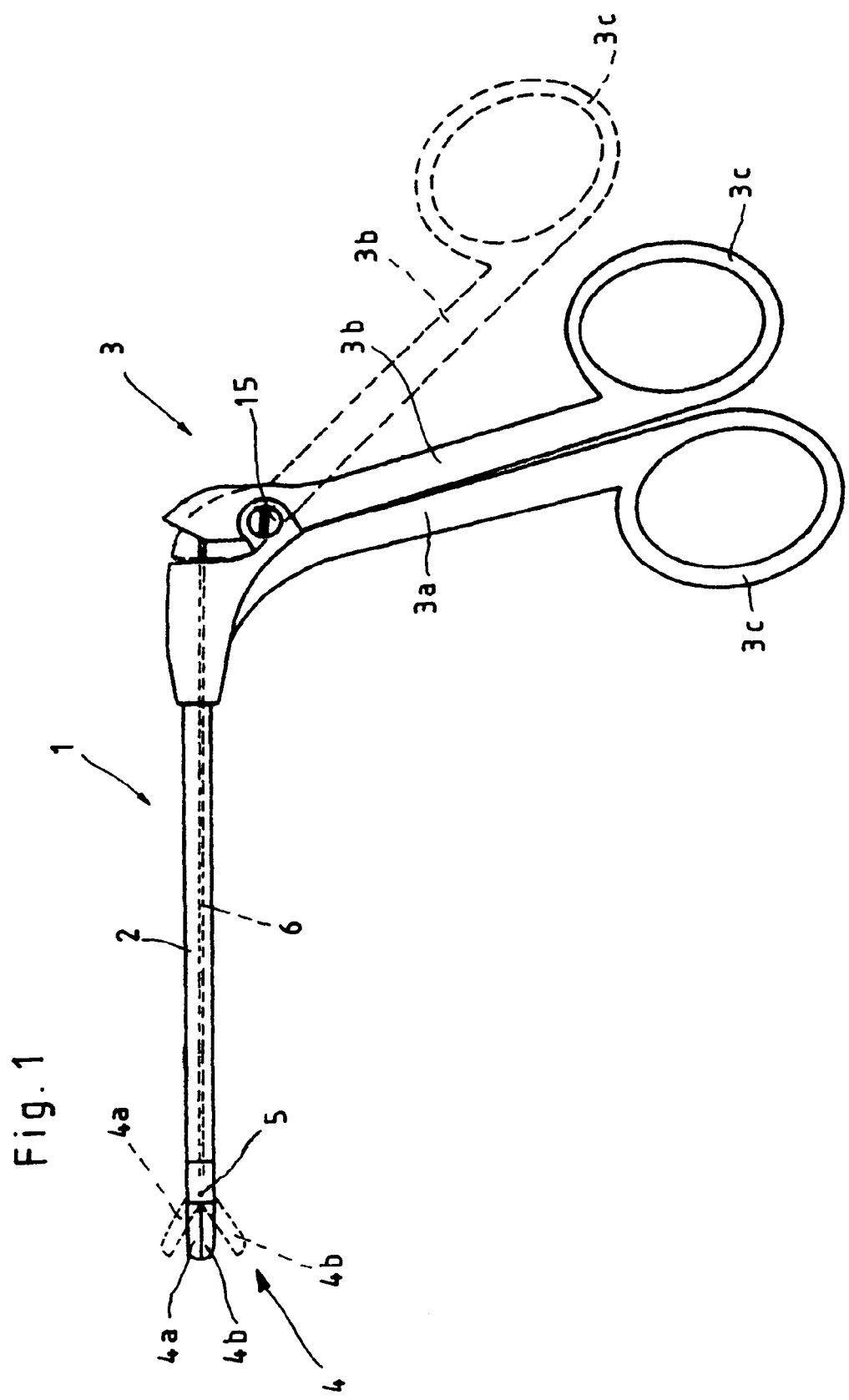

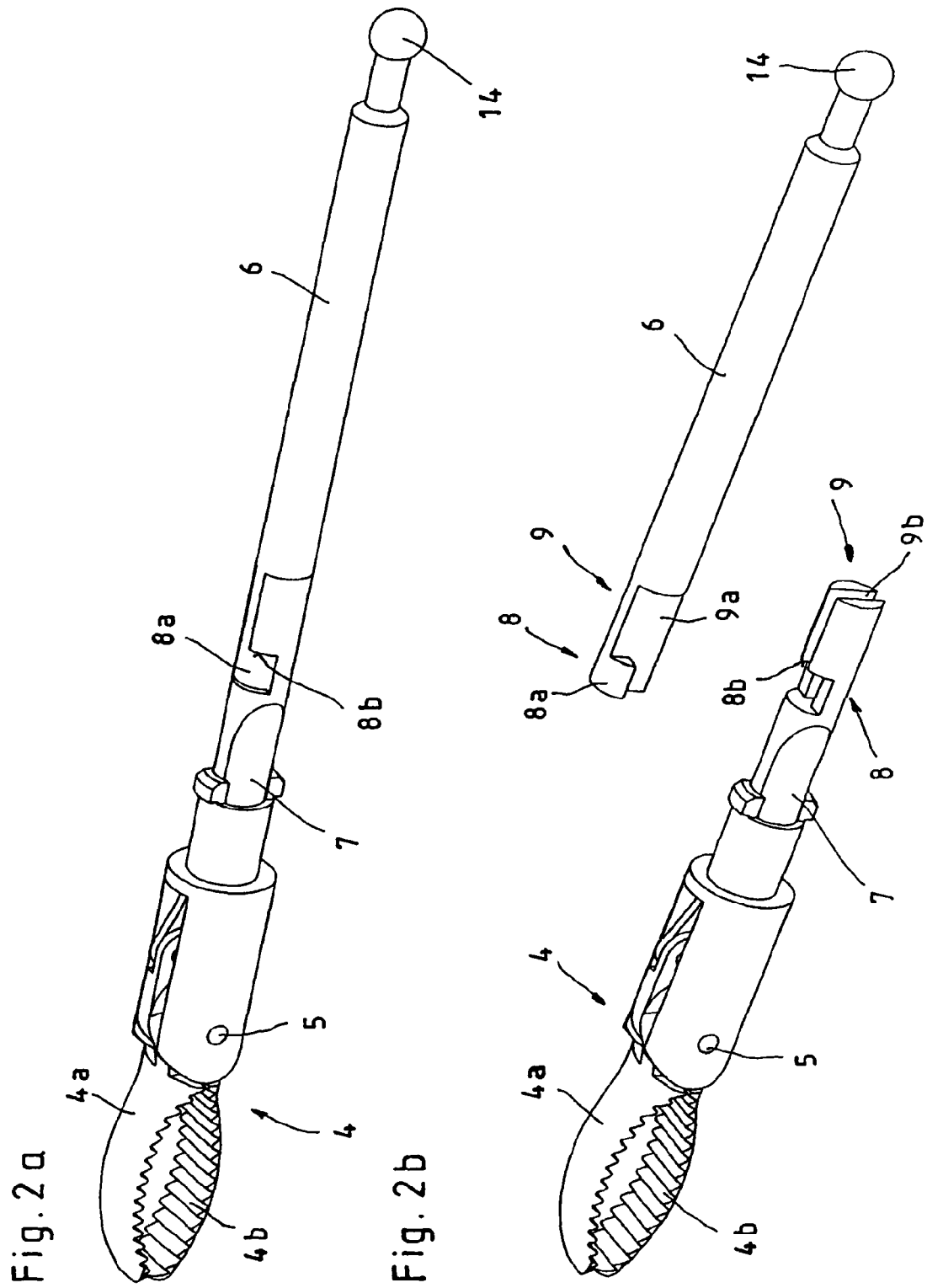

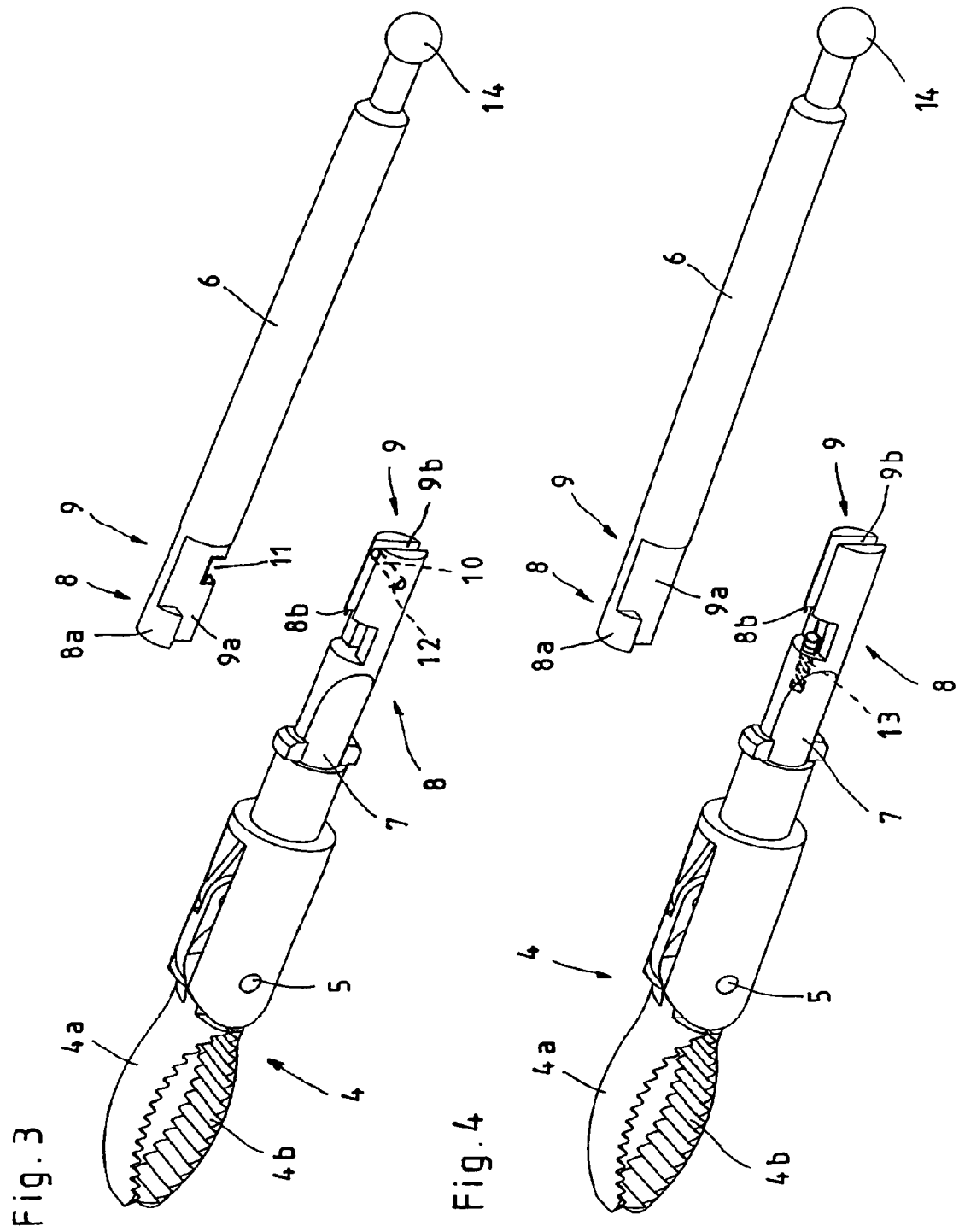

MEDICAL INSTRUMENT

CROSS-REFERENCE TO RELATED APPLICATIONS

The present application is continuation of U.S. patent application Ser. No. 10/662,759 filed on Sep. 15, 2003, now U.S. Pat. No. 7,691,126 which claims priority of German patent application 02 020 720.5 filed on Sep. 14, 2002.

FIELD OF THE INVENTION

The invention relates to a medical instrument with a shaft, a handle mounted on the proximal end of the shaft, and a tool mounted on the distal end of the shaft and capable of being activated by means of the handle, where the handle and the tool are in active connection by means of at least one activation rod.

BACKGROUND OF THE INVENTION

Conventional medical instrument are frequently used in practice as gripping, securing, and/or cutting tools. Thus, the jaw members can have blades for severing tissue or blunt surfaces for holding severed tissue, for instance, or stanching blood vessels.

In order to make the most flexible possible use of a medical instrument of this kind, on the one hand, and, on the other, to facilitate cleaning of the instrument, the known practice is to connect the tool detachably with the activation rod. The known connections between tool and activation rod, however, had the disadvantage that, as is known from EP 0577423 B1, they are of very expensive construction as screw-in or nesting connections, and thus simple, rapid, and thus cost-efficient tool replacement is not possible with these known instruments.

A conventional medical instrument is known from U.S. Pat. No. 5,496,347. In this known instrument, the activation rod is secured directly on the jaw members of the tool. For this purpose, the distal end of the activation rod has recesses into which cams configured on the jaw members engage. In order to secure the connection of the activation rod with the jaw members in the radial direction of the shaft, on the one hand the activation rod is mounted between the two jaw members and on the other hand the distal end of the shaft is configured so that the activation rod and the jaw members in this coupling area are surrounded by a housing, which is arranged inside the hollow shaft and in addition serves as a guide for the activation rod.

This known construction allows the tool to be secured on the activation rod without screwing connections; however, the complexity of installation—especially because of the use of the additional housing and the connection of the activation rod with the individual jaw members of the tool—is so great that, here too, simple, rapid, and thus cost-effective tool replacement is not possible with this instrument. Consequently it is the aim of the invention to design a medical instrument of the aforementioned type in such a way that the tool can be secured, especially as a one-way tool, simply and rapidly on the activation rod.

SUMMARY OF THE INVENTION

The aim is fulfilled according to the invention in that the tool has a tool shaft for purposes of securing it to the activation rod, and that the tool shaft and the activation rod, for purposes of securing them to one another, have protuberances and/or recesses, which can be engaged, at least partially as a form-locking connection, with corresponding recesses or protuberances of the other respective component.

Thanks to the invention's design of the coupling areas of the tool and activation rod, it is possible for the first time to secure the components that are to be joined together without additional securing elements, essentially by means of a socket connection. The flexibility of the instrument to be used with various tools is consequently increased because the protuberances and/or recesses for securing the activation rod to the tool are configured on a tool shaft of the tool.

To ensure the widest possible use of the inventive medical instrument, according to a preferred embodiment it is proposed that the tool should be able to be secured to the activation rod in such a way that forces in the longitudinal direction of the activation rod and/or torsion forces can be transmitted to the tool.

The tool and activation rod are connected preferably by means of a movement that is essentially perpendicular to the longitudinal axis of the activation rod, whereby this motion can be executed as an insertion motion in the direction perpendicular to the longitudinal axis of the activation rod or as a rotating motion around an axis perpendicular to the longitudinal axis of the activation rod.

It is also proposed with the invention that the tool should be detachably fixable to the tool. In this configuration, the tool shaft for instance can be used as an adapter in order to bring various tools with the adapter that has an identical activation rod connection into connection with the activation rod.

According to a preferred embodiment of the invention, the activation rod and the tool shaft are configured to have an essentially round cross-section. This configuration is particularly advantageous when torsion forces are to be transferred to the tool.

According to a first practical embodiment with essentially round cross-section of the activation rod and the tool shaft, in the area of the distal end of the round activation rod at least on one side a tangential leveling is configured on the activation rod in such a way that the distal end of the activation rod also has a head area that extends beyond the leveling in radial direction. The proximal area of the tool shaft thus has an overlapping for receiving the head area of the activation rod as well as a recess corresponding with the tangential leveling of the activation rod.

While it is possible, with the aforementioned embodiment, to configure the leveling asymmetrically, it is proposed according to a second alternative embodiment that the tangential leveling of the activation rod should be configured as a center rod leveled from two opposite sides and the corresponding recess on the tool shaft is configured as a radial slit.

It is further proposed with the invention that the activation rod and the tool can be coupled with one another by means of at least one stud running diagonally to the instrument longitudinal axis, where the stud is configured either on the activation rod or on the tool shaft and engages in a corresponding recess in the tool shaft or in the activation rod.

Use of the stud to connect the activation rod with the tool can thus be considered in addition or as an alternative to the configuration of the overlapping and of the head area.

It is, finally, proposed with the invention that a spring element should be included in order to transmit pulling or pushing forces in the coupling area between the activation rod and the tool. Besides the possibility of using the spring power of the spring element, for instance in order to open the tool in applying pushing pressure, the spring force reinforces the form-locking link of the activation rod and tool shaft components.

Additional characteristics and advantages of the invention can be seen from the following description of the associated illustrations, in which three embodiments of an inventive medical instrument are depicted schematically as examples. The illustrations are as follows:

BRIEF DESCRIPTION OF THE DRAWINGS

FIG. 1 is a schematic lateral view of an inventive medical instrument

FIG. 2a is a perspective lateral view of an activation rod and a tool according to a first embodiment of the invention in assembled condition.

FIG. 2b is a view according to FIG. 2a, but depicting the activation rod and the tool in a position detached from one another.

FIG. 3 is a view according to FIG. 2b, depicting a second embodiment of the invention FIG. 4 is a view according to FIG. 2b, depicting a third embodiment of the invention

DETAILED DESCRIPTION OF THE INVENTION

The illustration in FIG. 1 shows a lateral view of a medical instrument 1, whose power transmission mechanism can be used in many ways, such as for punching, cutting, as a needle holder, to secure instruments, and so on.

The illustrated medical instrument 1 consists essentially of a hollow shaft 2 having on its proximal end a handle 3 which consists of a rigid gripping member 3a and a gripping member 3b that can be rotated in relation to the rigid gripping member 3a. The distal end of the shaft 2 has a tool 4 which is made up of two jaw members 4a and 4b that can rotate with respect to one another around a common rotation point 5.

As can be seen from the views in FIGS. 2a to 4 in connection with the composite view of FIG. 1, the jaw members 4a and 4b of the tool 4 and the rotatable gripping member 3b of the handle 3 are connected with one another by means of an activation rod 6 in such a way that the jaw members 4a and 4b can be moved from the closed position (striped area in FIG. 1) into the open position (dotted section in FIG. 1) or vice versa by displacement of the gripping member 3b. The respective resulting position of the rotatable gripping member 3b is also striped in FIG. 1 (indicating the closed position) and dotted (for the open position).

The illustrations in FIGS. 2a to 4 also show that the activation rod 6 is not directly secured to the tool 4, but rather to a tool shaft 7, which in the illustrated embodiments is detachably connected with the tool 4 and in direct active connection with the jaw members 4a and 4b of the tool 4.

To connect the activation rod 6 with the tool shaft 7, the illustrated embodiments indicate, both on the activation rod 6 and on the tool shaft 7, protuberances 8 and recesses 9 which correspond with corresponding protuberances 8 and recesses 9 of the other respective component (6, 7 or 7, 6) in such a way that they can be brought together in form-locking engagement. In the illustrated embodiments, this mutually corresponding configuration of the protuberances 8 and recesses 9 can be seen especially in FIG. 2a, which shows a continuous round cross-section of activation rod 6 and tool shaft 7 when they are joined together. The activation rod 6 and the tool shaft 7 can also, of course, have cross-section shapes that are non-round and/or differ from one another.

In the embodiments illustrated in FIGS. 2a to 4, the recesses 9 on the activation rod 6 are formed by tangential levelings which are configured on two opposite sides on the activation rod 6 in such a way that the activation rod in the area of this leveling consists only of a narrow middle stud 9a. The distal end of the activation rod 6 forms a head area 8a which overhangs the middle stud 9a in radial direction and forms a protuberance 8.

To receive the middle stud 9a as well as the head area 8a of the activation rod 6, on the tool shaft 7 a radial slit is configured as a recess 9 and an overlapping 8b is configured as a protuberance 8. As can be seen from FIG. 2a, the respective protuberances 8 and recesses 9 of the activation rod 6 and tool shaft 7, when joined together, blend together in such a way that they are interlocking in a form-locking connection.

Alternatively to the illustrated embodiments, in which the recess 9 is configured on the activation rod 6 as a symmetrical two-sided leveling of the activation rod 6 forming the middle stud 9a, it is also possible of course to perform the leveling asymmetrically on just one side or on both sides to strongly varying degrees. The middle stud 9a can thus, as shown, be four-sided but can for instance have likewise a cross-section tapering in the insertion direction. It is also possible that the cross-section of the middle stud 9a changes in the axial direction.

The second embodiment shown in FIG. 3 differs from the one in FIG. 2b in that a stud 10 is also arranged in the tool shaft 7 running diagonally to the instrument longitudinal axis, which stud 10 engages in a corresponding recess 11 in the activation rod 6. In the illustrated embodiment the stud 10 is mounted in a hole 12 bored in the tool shaft 7. An alternative possibility is to install the stud 10 on the activation rod 6 and to configure the corresponding recess 11 on the tool shaft 7, so that it is also possible in both cases to configure the stud 10 as a single unit with the activation rod 6 or the tool shaft 7.

The third embodiment, illustrated in FIG. 4, differs from the one FIG. 2b in that a spring element 13 is mounted in the coupling area between the activation rod 6 and the tool 4. The spring element 13, sketched only as an example, can serve, for instance in applying pushing pressure, to open the tool 4 by spring action, or else to reinforce the form-locking joining of the components, i.e. activation rod 6 and tool shaft 7. If the spring element 13 is mounted between the tool 4 and the tool shaft 7, the spring element 13 can cause an activation of the tool 4 entirely in a single direction (opening or closing). The other corresponding motion (closing or opening) can then be produced by the activation of the activation rod 6.

In particular in the configuration of the coupling area between the activation rod 6 and the tool 4 with a spring element 13, it is possible to dispense with the head area 8a shown in FIGS. 2a to 4 on the activation rod 6.

In this case no pulling force can be transmitted to the tool 4 by means of the activation rod 6, but only pushing and torsion forces. The pulling forces in this embodiment can be assumed by the spring element 13, whose spring force closes the tool 4 or whose spring force must be overcome by means of the pushing force applied by means of the activation rod 6 to open the tool 4.

Of course, construction solutions are also possible in which a pulling force is applied by means of the activation rod 6 and the pushing force is produced by the spring power of the spring element 13.

The medical instrument 1 is activated as follows: First, from the separated starting position illustrated in FIG. 2b, the activation rod 6 and the tool shaft 7, by means of a motion essentially perpendicular to the longitudinal axis of the activation rod 6, are brought into engagement with one another by matching the reciprocal protuberances 8 and recesses 9 so as to produce the joined configuration illustrated in FIG. 2a.

Then the activation rod 6 with the proximal end in front is introduced into the hollow shaft 2. To connect the activation rod 6 with the rotatable gripping member 3b of the handle 3, on the proximal end of the activation rod 6 a toggle head 14 is arranged which can be inserted to engage with a corresponding spherical recess (not illustrated) on the gripping member 3b.

For secure action of the gripping members 3a, 3b of the handle 3, the handles have finger loops 3c on their free ends. In the illustrated embodiment the gripping member 3b can be rotated around a rotation axis 15 with respect to the other, rigid gripping member 3a.

Through the coupling of the rotatable gripping member 3b by the activation rod 6 with the tool 4, the jaw members 4a, 4b of the tool 4 open and close.

Thanks to the simple coupling of the activation rod 6 on the tool 4 or the tool shaft 7 by the formation of the protuberances 8 and recesses 9, new tools 4 can be especially simply and quickly secured on the activation rod 6, so that the use of one-time tools is particularly facilitated.

The coupling of the activation rod 6 on the tool 4 or tool shaft 7 is, in addition, configured in such a way that forces can be transmitted in longitudinal direction of the activation rod 6 and torsion forces can be transmitted on the tool 4.

What is claimed is:

1. A medical instrument comprising a shaft, a handle mounted on the proximal end of the shaft, and a tool mounted on the distal end of the shaft and activated by the handle, where the handle and the tool are in active connection by means of at least one activation rod and the tool adapted to be secured detachably by means of a tool shaft on the activation rod, for which purpose both the tool shaft and the activation rod have protuberances and recesses, which can be joined at least partially in a form-locking connection, with corresponding recesses and protuberances of the other of the tool shaft or activation rod, wherein the recesses and protuberances corresponding to one another are configured in such a way that the tool shaft and the activation rod are adapted to be brought into engagement with one another by means of a movement exclusively in a direction essentially perpendicular to the longitudinal axis of the activation rod, and that the tool shaft and the activation rod coupled to one another are nonmoveably fixed relative to one another in all other directions.

2. The medical instrument according to claim 1, wherein the tool can be secured to the activation rod in such a way that forces can be transmitted in the longitudinal direction of the activation rod and/or torsion forces can be transmitted to the tool.

3. The medical instrument according to claim 2, wherein the tool and the activation rod can be connected with one another by means of a motion essentially perpendicular to the longitudinal axis of the activation rod.

4. The medical instrument according to claim 3, wherein the activation rod and the tool shaft are configured as essentially round in cross-section.

5. The medical instrument according to claim 4, wherein in the area of the distal end of the round activation rod at least on one side a tangential leveling is formed on the activation rod in such a way that the distal end of the activation rod further has a head area overhanging the leveling in radial direction and the proximal area of the tool shaft has an overlap for receiving the head are of the activation rod and a recess corresponding to the tangential leveling of the activation rod.

6. The medical instrument according to claim 5, wherein the tangential leveling of the activation rod is configured as a middle stud leveled from two opposite sides and the corresponding recess on the tool shaft is configured as a radial slit.

7. Medical instrument according to claim 6, wherein the activation rod and the tool can be coupled to one another by means of at least one stud running diagonally to the instrument longitudinal axis, where the stud on the one hand is stored in a hold bored in the activation rod or in the tool shaft and on the other hand engages in a corresponding recess in the tool shaft or in the activation rod.

8. Medical instrument according to claim 7, wherein, for the transmission of pulling or pushing forces in the coupling area, a spring element is placed between the activation rod and the tool.

9. Medical instrument according to claim 8, wherein the tool can be activated by means of the spring element.

* * * * *